US012559711B2

(12) United States Patent (10) Patent No.: US 12,559,711 B2
Govyadinov et al. (45) Date of Patent: Feb. 24, 2026

(54) THERMAL CELL LYSIS CHAMBER WITH LYSIS CONTROL CIRCUITRY

(71) Applicant: HEWLETT-PACKARD DEVELOPMENT COMPANY, L.P., Spring, TX (US)

(72) Inventors: Alexander Govyadinov, Corvallis, OR (US); Viktor Shkolnikov, Palo Alto, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 937 days.

(21) Appl. No.: 17/782,601

(22) PCT Filed: Jan. 23, 2020

(86) PCT No.: PCT/US2020/014772
§ 371 (c)(1),
(2) Date: Jun. 3, 2022

(87) PCT Pub. No.: WO2021/150225
PCT Pub. Date: Jul. 29, 2021

(65) Prior Publication Data
US 2023/0011683 A1 Jan. 12, 2023

(51) Int. Cl.
*C12M 1/00* (2006.01)
*B01L 3/00* (2006.01)
(Continued)

(52) U.S. Cl.
CPC ....... *C12M 47/06* (2013.01); *B01L 3/502761* (2013.01); *B01L 2200/147* (2013.01);
(Continued)

(58) Field of Classification Search
None
See application file for complete search history.

(56) References Cited

U.S. PATENT DOCUMENTS 6,815,209 B2 * 11/2004 Baeummer ............ C12N 13/00
436/63
2003/0075446 A1 4/2003 Culbertson
(Continued)

FOREIGN PATENT DOCUMENTS

EP 1314472 A1 5/2003
EP 1876231 B1 8/2016

OTHER PUBLICATIONS

Ke et al: "Single step cell lysis/PCR detection of *Escherichia coli* in an independently controllable silicon microreactor", Sensors and Actuators B, vol. 120, No. 2, 2007, pp. 538-544.
(Continued)

*Primary Examiner* — Elizabeth A Robinson
*Assistant Examiner* — Brittany I Fisher
(74) *Attorney, Agent, or Firm* — Foley & Lardner LLP

(57) ABSTRACT

An example apparatus comprises a thermal cell lysis chamber, including a substrate and a lid coupled to the substrate to form a microfluidic channel therethrough. The apparatus includes cell detection circuitry to detect presence of a cell within the microfluidic channel and to detect lysis of the cell. The apparatus also includes a thermal lysing element disposed in the lid to apply heat to a cell detected by the cell detection circuitry, and lysis control circuitry. The lysis control circuitry is to regulate a temperature applied by the thermal lysing element, based on detection by the cell detection circuitry of a cell within the microfluidic channel and based on detection by the cell detection circuitry of a lysis event, and record the temperature applied by the thermal lysing element at which the lysis event occurred.

4 Claims, 13 Drawing Sheets

(51) Int. Cl.
    *C12M 1/34*         (2006.01)
    *C12M 3/06*         (2006.01)
    *C12N 1/06*         (2006.01)

(52) U.S. Cl.
    CPC .................. *B01L 2300/0654* (2013.01); *B01L 2300/1827* (2013.01); *B01L 2400/0487* (2013.01)

(56) References Cited

U.S. PATENT DOCUMENTS

| | | |
|---|---|---|
| 2008/0305467 A1 | 12/2008 | Ussing |
| 2013/0143197 A1 | 6/2013 | Heyneker |
| 2015/0018226 A1 | 1/2015 | Hansen et al. |
| 2017/0283859 A1 | 10/2017 | Lin et al. |
| 2017/0304829 A1* | 10/2017 | Andreyev .............. C12Q 1/686 |
| 2018/0021777 A1* | 1/2018 | Giri ................... B01L 3/502715 |
| | | 422/73 |
| 2019/0048309 A1 | 2/2019 | Govyadinov |
| 2019/0136226 A1* | 5/2019 | Swenson ................. C12Q 1/37 |
| 2019/0151848 A1* | 5/2019 | Nielsen ................ B01L 3/0268 |
| 2019/0323069 A1 | 10/2019 | Cao |

OTHER PUBLICATIONS

Seung-Ki Baek et al: "Wireless induction heating in a microfluidic device for cell lysis", Lab Chip, vol. 10, Jan. 2010, pp. 909-917.

* cited by examiner

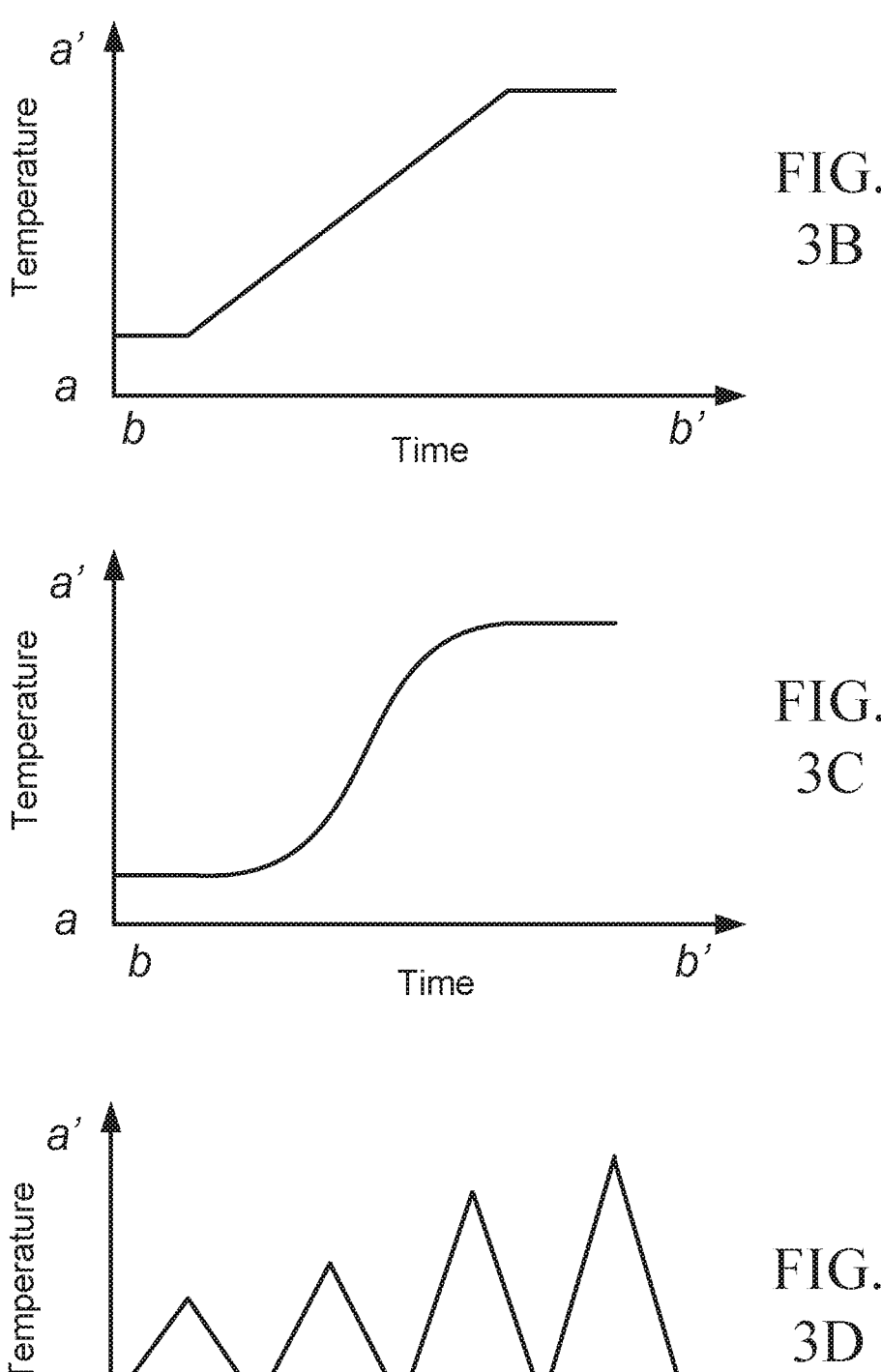
FIG.
3B
FIG.
3C
FIG.
3D

THERMAL CELL LYSIS CHAMBER WITH LYSIS CONTROL CIRCUITRY

CROSS-REFERENCE TO RELATED APPLICATIONS

This application is a U.S. National Stage filing under 35 U.S.C. § 371 of PCT Application No. PCT/US2020/014772, filed Jan. 23, 2020, incorporated by reference herein.

BACKGROUND

Significant efforts are being expended on making diagnostic technologies usable and relevant in point-of-need and point-of-care (POC) settings. Microfluidic technologies have several advantages in this context, including small sample and device size, low power and fast assay times. Development of new diagnostic platforms that incorporate lab-on-a-chip technologies for portable assays is driving the need for rapid, simple, low cost methods to prepare samples for downstream processing or detection. An important component of the sample preparation process is cell lysis. A range of approaches have been attempted to miniaturize and adapt lysis methods for downstream microfluidic molecular detection of nucleic acids.

BRIEF DESCRIPTION OF THE DRAWINGS

FIG. 3B illustrates another example of temperature ramping implemented by lysis control circuitry, according to the present disclosure.

FIG. 3C illustrates another example of temperature ramping implemented by lysis control circuitry, according to the present disclosure.

FIG. 3D illustrates another example of temperature ramping implemented by lysis control circuitry, according to the present disclosure.

DETAILED DESCRIPTION

Figures 1A, 1B, 1C:
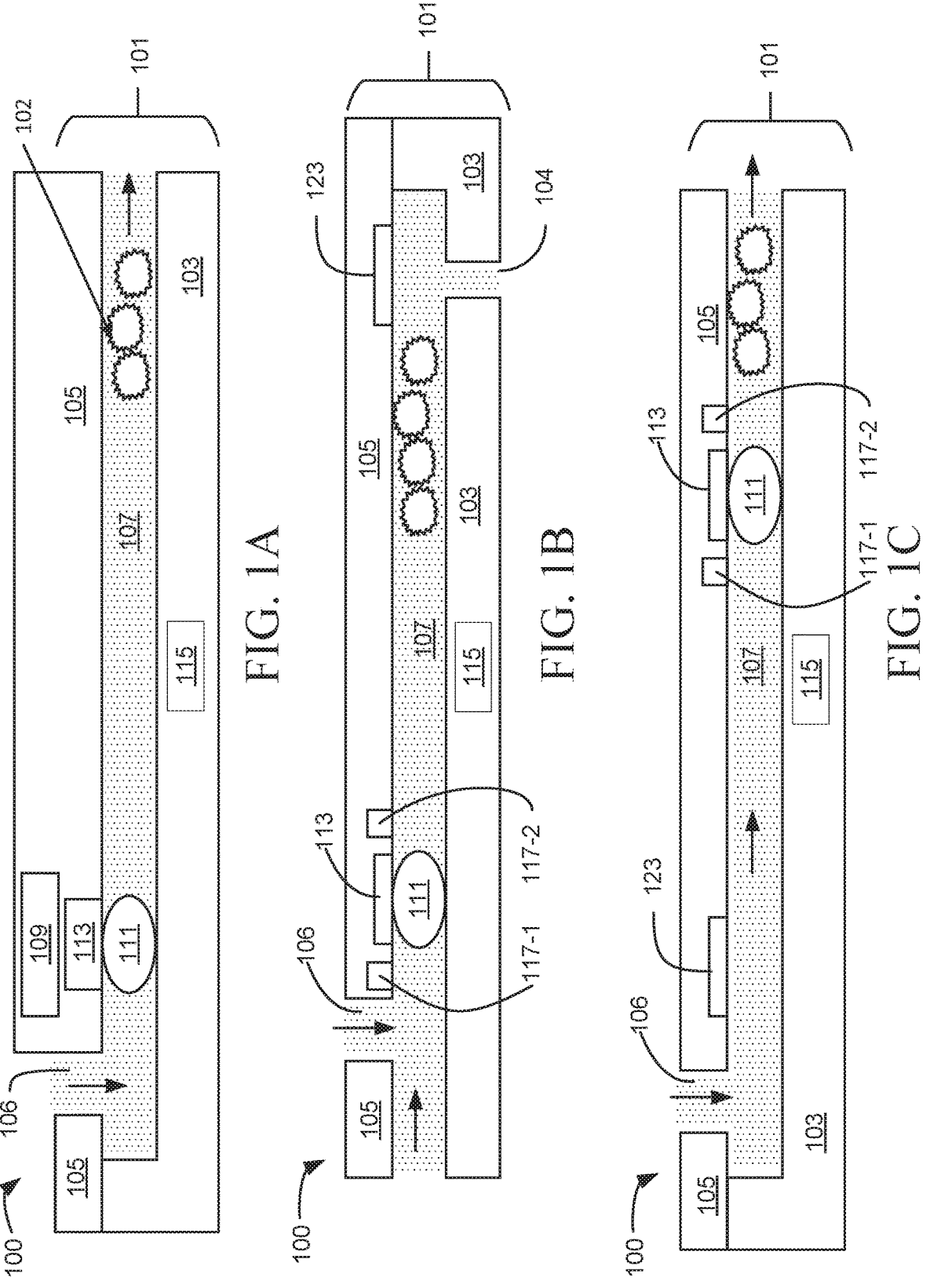
FIG. 1A illustrates an example apparatus including a thermal cell lysis chamber and lysis control circuitry, according to the present disclosure.
FIG. 1B illustrates an example apparatus including a thermal cell lysis chamber including a fluid output and lysis control circuitry, according to the present disclosure.
FIG. 1C illustrates an example apparatus including a thermal cell lysis chamber including a fluidic pump and lysis control circuitry, according to the present disclosure.

In the following detailed description, reference is made to the accompanying drawings which form a part hereof, and in which is shown by way of illustration specific examples in which the disclosure may be practiced. It is to be understood that other examples may be utilized, and structural or logical changes may be made without departing from the scope of the present disclosure. The following detailed description, therefore, is not to be taken in a limiting sense, and the scope of the present disclosure is defined by the appended claims. It is to be understood that features of the various examples described herein may be combined, in part or whole, with each other, unless specifically noted otherwise.

Biological cells are the basic building blocks of skin, tissues, and other materials. Cells and their organelles are enveloped by thin membranes that separate their chemical contents from the extracellular environment. Biological membranes are supramolecular assemblies composed of a lipid double layer with embedded and adsorbed membrane proteins. Each monolayer of the membrane consists of billions of adjacent lipid molecules, which are composed of two hydrophobic tails and a hydrophilic headgroup. The two monolayers taken together, facing each other with the hydrophobic tails, serve as a barrier of 3-5 nm thickness, which exhibits a partial permeability to some small hydrophobic and polar molecules.

Cell lysis temperature is strongly controlled by cell membrane composition, and therefore can be a marker for cell membrane composition. Cells can be differentiated by cell membrane composition and cell membrane composition serves as a marker of other cellular processes, including metabolism. There are also over 100 genetic diseases that are related to cell membrane lipids. For instance, cell deformability is an emerging biomarker for cancer: cancer cells tend to be softer compared to theft benign counterparts Thus there is a desire to measure and characterize cell membrane composition of cell populations. Membrane thermal properties and membrane fluidity are not measured in flow cytometry. However, the temperature at which a cell ruptures (e.g., the cell lysis temperature) can be used differentiate cells and can be used to identify certain clinical conditions.

In accordance with the present disclosure, an apparatus may quickly release intracellular nucleic acids and proteins without the need for additional reagents or beads. An example apparatus comprises a thermal cell lysis chamber, including a substrate and a lid coupled to the substrate to form a microfluidic channel therethrough. The apparatus includes cell detection element to detect presence of a cell within the microfluidic channel and to detect lysis of the cell. The apparatus also includes a thermal lysing element disposed in the lid to apply heat to a cell detected by the cell detection element, and lysis control circuitry. The lysis control circuitry is to regulate a temperature applied by the thermal lysing element, based on detection by the cell detection element of a cell within the microfluidic channel and based on detection by the cell detection element of a lysis event, and record the temperature applied by the thermal lysing element at which the lysis event occurred.

In another example, an apparatus comprises a cell reservoir to store a biologic sample including a plurality of cells, and a thermal cell lysis chamber coupled to the cell reservoir, the thermal cell lysis chamber including a substrate and a lid coupled to the substrate to form a microfluidic channel therethrough. The apparatus further includes a fluidic pump disposed within the thermal cell lysis chamber to move the biologic sample from the cell reservoir into the thermal cell lysis chamber. The apparatus also includes lysis control circuitry to regulate a temperature applied to a cell within the microfluidic channel, and record the temperature applied by the thermal lysing element at which lysis of the cell occurred.

Turning now to the figures, FIGS. 1A, 1B, and 10 illustrate examples of a thermal cell lysis chamber with lysis control circuitry, according to the present disclosure. Particularly, FIG. 1A illustrates an example apparatus including a thermal cell lysis chamber and lysis control circuitry. As illustrated in FIG. 1A, an apparatus 100, comprises a thermal cell lysis chamber 101, including a substrate 103 and a lid 105 coupled to the substrate 103 to form a microfluidic channel 107 therethrough. For instance, a reaction fluid including a biologic sample may be input to the apparatus 100 via fluid input 106. The reaction fluid flows through the thermal cell lysis chamber 101, until a cell is detected by cell detection element 109.

In various examples, a thermal lysing element 113 disposed in the lid 105 is to apply heat to a cell 111 detected by the cell detection element 109. For instance, in various examples, the apparatus 100 includes cell detection element 109 to detect presence of a cell 111 within the microfluidic channel 107 and to detect lysis of the cell 111. Lysis control circuitry 115 is to regulate a temperature applied by the thermal lysing element 113, based on detection by the cell detection element 109 of a cell 111 within the microfluidic channel 107 and based on detection by the cell detection element 109 of a lysis event. The lysis control circuitry 115 may also record the temperature applied by the thermal lysing element 113 at which the lysis event occurred. As used herein, a lysis event refers to or includes the moment at which rupture of a cellular membrane occurs. Once the cell 111 is lysed and the cellular materials 102 are released, the cellular materials 102 may proceed out of the apparatus 100 for down-stream processing, such as encapsulation. As discussed further herein, the lysis control circuitry 115 includes instructions, executable by a processing resource to control the temperature applied by the thermal lysing element 113, and to record the temperature at which lysis occurs.

FIG. 1B illustrates an example apparatus including a thermal cell lysis chamber including a fluid output and lysis control circuitry, according to the present disclosure. In the particular example illustrated in FIG. 1B, the cell detection element 109 includes a pair of impedance sensors 117-1, 117-2 to detect presence of a cell 111 within the microfluidic channel 107 responsive to a rapid increase in the impedance measured by the pair of impedance sensors 117-1, 117-2. As illustrated, the thermal lysing element 113 is disposed in the lid 105 between the pair of impedance sensors 117-1, 117-2. In such examples, the lysis control circuitry 115 is to instruct the thermal lysing element 113 to apply heat to the detected cell 111. As discussed herein, the temperature may increase in a variety of manners until lysis occurs. Accordingly, the cell detection element 109 includes a pair of impedance sensors 117-1, 117-2 to detect lysis of a detected cell 111 responsive to a rapid decline in the impedance measured by the pair of impedance sensors 117-1, 117-2. As an illustration, the lysis control circuitry 115 is to gradually increase the temperature applied by the thermal lysing element 113 and record the impedance across the microfluidic channel 107 at each temperature applied by the thermal lysing element 113. Once the lysis event is detected by the impedance sensors 117-1 and 117-2, the temperature at which the event was detected may be recorded by the lysis control circuitry 115.

In the example illustrated in FIG. 1B, an external pump may be used to push the fluid through the thermal cell lysis chamber 101. Similarly, an external pump may be used in FIG. 1A. In the example illustrated in FIG. 1B, fluid motion may be enabled by drop ejection via nozzle 104 by actuating a resistor, such as internal fluidic pump 123. Accordingly, an internal fluidic pump 123 may eject fluid out of the thermal cell lysis chamber 101 via nozzle 104. Once the cellular materials 102 are ejected via nozzle 104, the cellular materials 102 may proceed to additional components, including a PCR microreactor, for further processing.

In various examples, an external pump and/or an internal pump may be used to move the fluid through the thermal cell lysis chamber 101. As illustrated in FIG. 1B, the apparatus may include an internal fluidic pump 123. The fluidic pump 123 may comprise a resistor, such as a thermal inkjet resistor. Similarly, the thermal lysing element 113 may comprise a resistor, such as a thermal inkjet resistor. The electrical activation of thermal lysing element 113 results in heat applied to cell 111, whereas electrical activation of fluidic pump 123 results in the ejection of fluid via nozzle 104. The apparatus 100 illustrated in FIG. 1B may also include an external pump (not illustrated). While cellular material enters the thermal cell lysis chamber 101 via fluid input 106, a pump such as a thermal inkjet (TIJ) resistor disposed on an end of the apparatus 100 opposite of the nozzle 104 may push fluid through the thermal cell lysis chamber 101 by ejecting the fluid from nozzle 104.

In some examples, the thermal lysing element 113 is to operate as both a fluidic pump and a heating element. For instance, in such examples, the lysis control circuitry 115 is to instruct the thermal lysing element 113 (e.g., fluidic pump) to operate as a pump to move cellular material through the microfluidic channel 107. The lysis control circuitry 115 is also to instruct the thermal lysing element 113 to stop pumping responsive to detection of a cell 111 within the microfluidic channel 107 by impedance sensors 117-1 and 117-2, and to apply heat to the detected cell 111 at the temperature specified by the lysis control circuitry 115. As such, lysis control circuitry 115 may function as both a pump and a heating element.

FIG. 10 illustrates an example apparatus including a thermal cell lysis chamber including a fluidic pump and lysis control circuitry, according to the present disclosure. In the example illustrated in FIG. 1C, fluid pumping from a cell source is done using a fluidic pump 123. The fluidic pump 123 pulls the cells into the microfluidic channel 107 via fluid input 106, and subsequently pushes the cell 111 toward thermal lysing element 113. Thermal lysing element 113 also includes a resistor, as discussed with regards to FIG. 1B. In various examples discussed herein (such as FIGS. 6A and 6B, among others), the cell detection element includes a photodetector to optically detect the presence of a cell 111 within the microfluidic channel 107, and to detect a lysis event by visually observing rupture of the cellular membrane.

Figures 2, 3A:
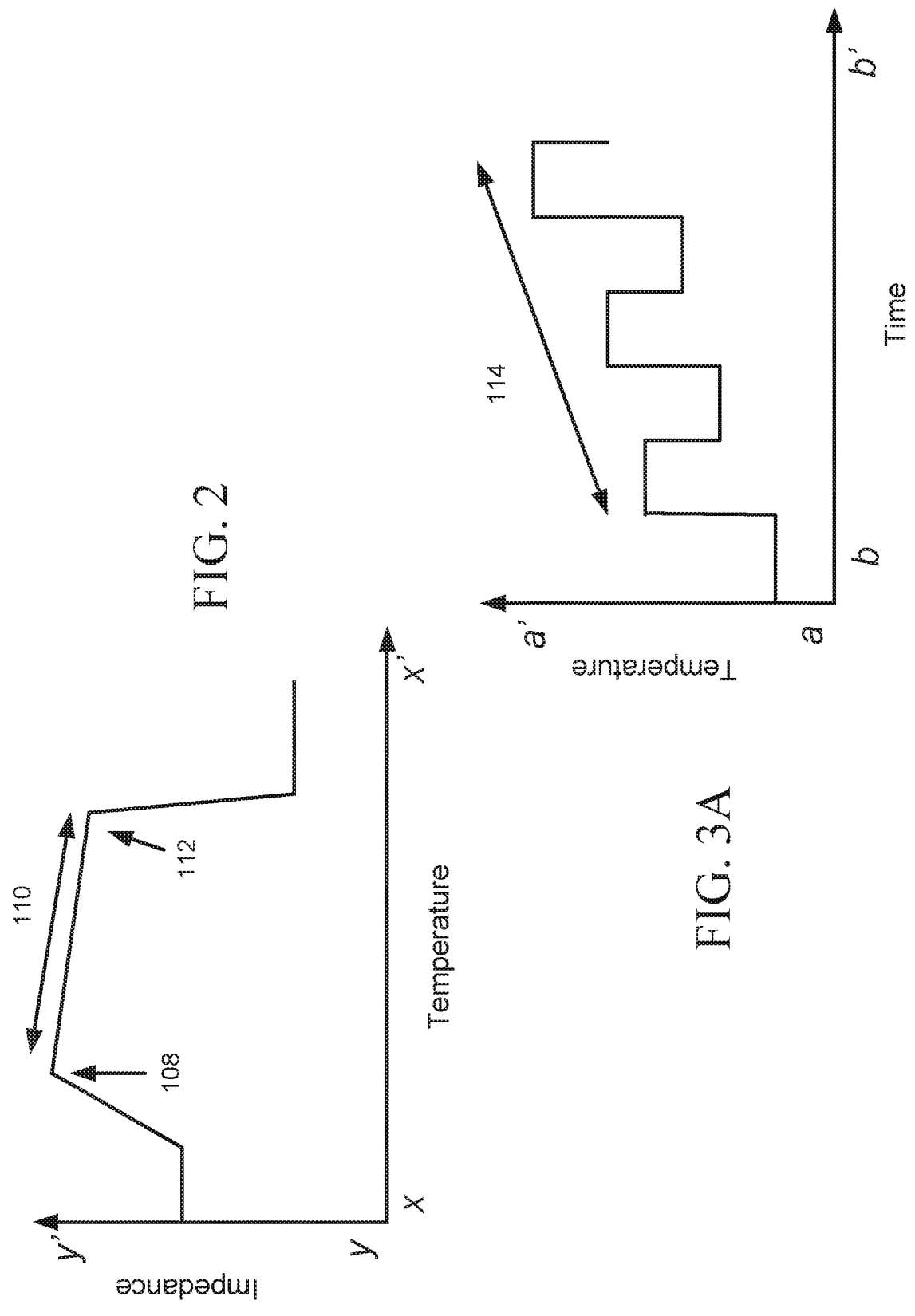
FIG. 2 illustrates an example change in impedance measurements as a function of temperature, according to the present disclosure.
FIG. 3A illustrates an example of temperature ramping implemented by lysis control circuitry, according to the present disclosure.

FIG. 2 illustrates an example change in impedance measurements as a function of temperature, according to the present disclosure. As illustrated in FIG. 2, temperature increases from x to x', and impedance increases from y to y'. A cell is detected at event 108, which causes a significant increase of impedance. A cell with an intact cellular membrane will block the electrodes (e.g., 117-1 and 117-2 illustrated in FIGS. 1B and 10), and impedance will drastically increase. Over the span of 110, as the temperature is increasing, the impedance slowly decreases until 112, at which point the impedance drastically decreases. As the cell is heated, pores form in the cellular membrane which results in the impedance of the cell gradually decreasing by a small amount. As the cellular membrane ruptures (e.g., is lysed), the cell releases ionic content into the microfluidic channel 107, and impedance abruptly falls at event 112. The point at which the impedance drastically decreases is the point at which the cell has ruptured, and the information is recorded by the lysis control circuitry 115.

FIG. 3A illustrates an example of temperature ramping implemented by lysis control circuitry, according to the present disclosure. Various example methods may be implemented to monitor the change of temperature and rupture of the cellular membrane. Referring to FIG. 3A, the temperature increases from a to a', and time increases from b to b'. As time progresses from b to b', the temperature may ramp up in increments as illustrated, throughout time span 114. Once cell rupture is detected, temperature increases cease as the cellular contents progress through the microfluidic channel for further processing.

FIG. 3B illustrates another example of temperature ramping implemented by lysis control circuitry, according to the present disclosure. In the example illustrated in FIG. 3B, time increases from b to b', and temperature increases from a to a'. As time progresses from b to b', temperature gradually increases at a constant rate from a to a' until a lysis event is detected, at which point the temperature plateaus.

FIG. 3C illustrates another example of temperature ramping implemented by lysis control circuitry, according to the present disclosure. Particularly, FIG. 3C illustrates method in which temperature increases at an increasing rate from a to a' until a lysis event is detected. Again, temperature increases from a to a' as time progresses from b to b', but as opposed to the example illustrated in FIG. 3B, the rate of temperature change rapidly increases until the lysis event.

FIG. 3D illustrates another example of temperature ramping implemented by lysis control circuitry, according to the present disclosure. Particularly, FIG. 3D illustrates an interval scaling method. As illustrated in FIG. 3D, temperature increases and decreases in intervals as time progresses from b to b'. As opposed to the example illustrated in FIG. 3A, as time progresses, the peak temperature increases. The thermal lysing element 113 will increase the temperature applied to the cell 111, and then decrease the temperature applied to the cell 111. Each time the temperature increases again, the peak temperature reached by the thermal lysing element 113 is higher than the last temperature increase, until a lysis event is detected.

As temperature applied by the thermal lysing element 113 increase, pores in the membrane of cell 111 open, and the size and density of pores in the membrane of cell 111 increases. This increase in size and density of cellular pores can be detected by a shift in impedance spectra via impedance spectroscopy in the range of 10 kHz to 500 megahertz (MHz). This increase in size and density of cellular pores can also be detected by light scattering optics, by observing the cell surface.

When impedance spectroscopy infers that pore size is large (and therefore cell is close to lysing) temperature ramp rate is slowed down to obtain a more precise reading on lysis. When light scattering infers that pore size is large (and therefore cell is close to lysing) temperature ramp rate is slowed down to obtain a more precise reading on lysis.

Figures 4A, 4B, 4C:
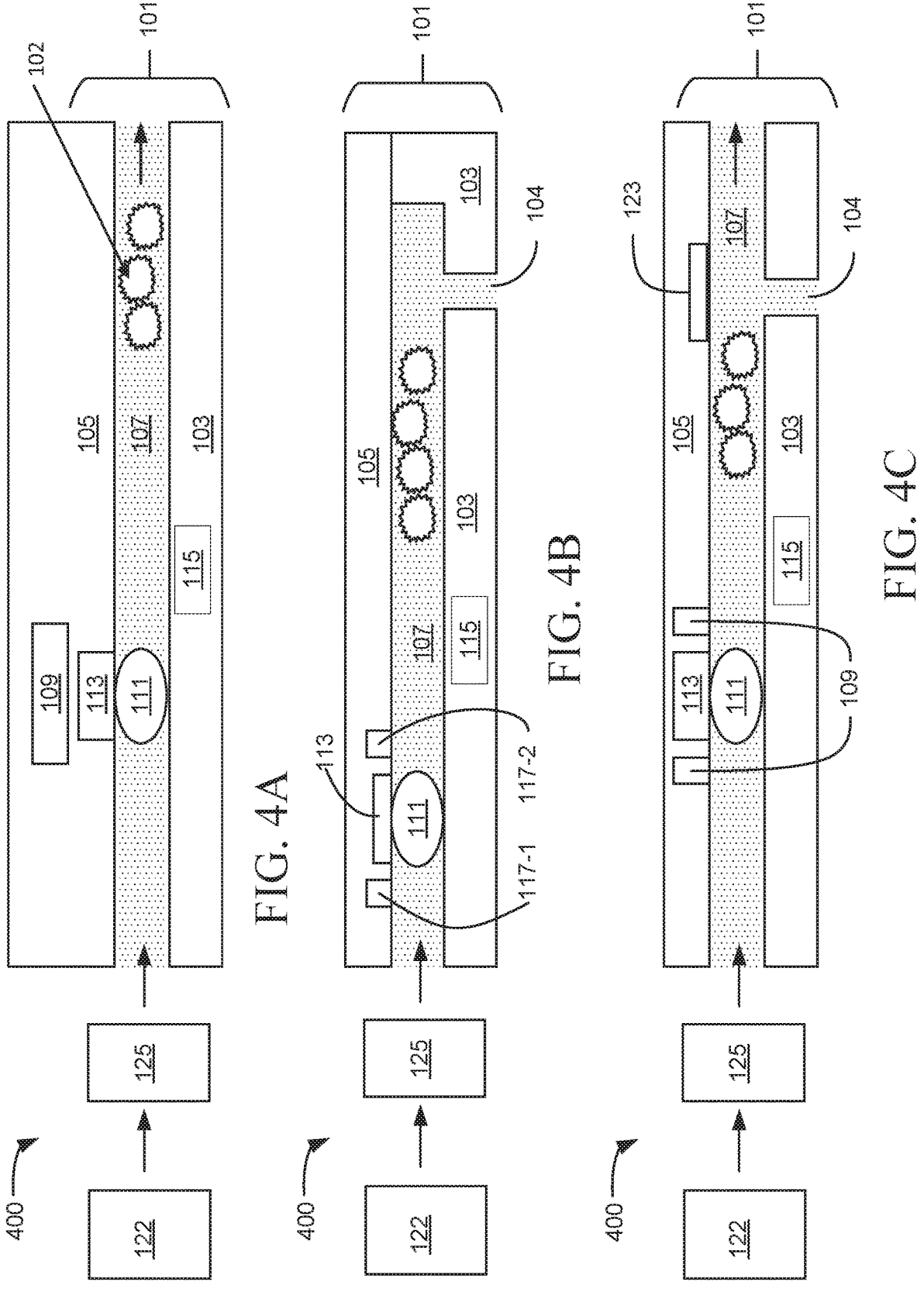
FIG. 4A illustrates an example apparatus with an external cell reservoir, according to the present disclosure.
FIG. 4B illustrates an example apparatus with an external cell reservoir and a fluid output, according to the present disclosure.
FIG. 4C illustrates an example apparatus with an external cell reservoir and a fluid output, according to the present disclosure.

FIGS. 4A, 4B, and 4C illustrate example apparatuses with external cell reservoirs, according to the present disclosure. FIG. 4A illustrates an apparatus 400, comprising a cell reservoir 122 to store a biologic sample including a plurality of cells, and an external pump 125 to push the cell 111 through the microfluidic channel 107. In additional and/or alternative examples, the apparatus 400 includes a fluidic pump disposed within the thermal cell lysis chamber 101 (see for instance, fluidic pump 123 illustrated in FIG. 10) to move the biologic sample from the cell reservoir 122 into the thermal cell lysis chamber 101. The thermal cell lysis chamber 101 is coupled to the cell reservoir 122, and the thermal cell lysis chamber 101 includes a substrate 103 and a lid 105 coupled to the substrate 103 to form a microfluidic channel 107 there through. As discussed with regards to FIGS. 1A, 1B, and 1C, the apparatus 400 further includes lysis control circuitry 115 to regulate a temperature applied to a cell 111 within the microfluidic channel 107, and record the temperature applied by the thermal lysing element 113 at which lysis of the cell 111 occurred.

The flow of cells from cell reservoir 122 through microfluidic channel 107 may change based on detected cellular events. For instance, in various examples, the lysis control circuitry 115 is to instruct the fluidic pump 125 to stop pumping responsive to detection of a cell 111 within the microfluidic channel 107 by cell detection element 109, and to resume pumping responsive to detection of a lysis event by the cell detection element 109. When an internal fluidic pump is used (such as fluidic pump 123 illustrated in FIG. 10), the lysis control circuitry 115 is to instruct the fluidic pump 123 to stop pumping responsive to detection of a cell 111 within the microfluidic channel 107 by cell detection element 109, and to resume pumping responsive to detection of a lysis event by the cell detection element 109. In various examples, the apparatus 400 includes a thermal lysing element 113 disposed in the lid 105 to apply heat to a cell 111 detected by the cell detection element 109. The lysis control circuitry 115 is to gradually increase the temperature applied by the thermal lysing element 113 until lysis of the cell 111 is detected, as discussed with regards to FIGS. 3A, 3B, 3C, and 3D.

As a further example, the apparatus 400 includes a thermal lysing element 113 disposed in the lid 105 to apply heat to a cell 111 detected by the cell detection element 109, the lysis control circuitry 115 to increase the temperature applied by the thermal lysing element 113 in discrete temperature increases until lysis of the cell 111 is detected.

FIG. 4B illustrates an example apparatus with an external cell reservoir and a fluid output, according to the present disclosure. In various examples, one side of the microfluidic channel 107 may be closed. For instance, referring to FIG. 4B, fluid flows in from the cell reservoir 122, into fluidic pump 125, and drawn into the thermal cell lysis chamber 101. As discussed herein, a cell 111 can be detected by the impedance sensors 117-1, 117-2, and then heated by thermal lysing element 113. When the cell 111 is lysed, the cellular materials 102 may be dispensed via nozzle 104, such as to polymerase chain reaction (PCR) analysis components.

FIG. 4C illustrates an example apparatus with an external cell reservoir and a fluid output, according to the present disclosure. As illustrated in FIG. 4C, fluid flows in from the cell reservoir 122, into fluidic pump 125, and drawn into the thermal cell lysis chamber 101. A cell 111 can be detected by cell detection element 109, which may include impedance sensors or optical sensors, and then heated by thermal lysing element 113. When the cell 111 is lysed, the cellular materials 102 may be dispensed via nozzle 104 and/or via the end of the thermal cell lysis chamber 101 opposite the cell reservoir 122. Like in FIG. 1B, cell products can be ejected via nozzle 104 by TIJ resistor (123) for further analysis. While various examples are described herein with an external pump, examples are not so limited. The pump may be integrated into the apparatus, as discussed further with regards to FIGS. 5A and 5B.

Figures 5A, 5B:
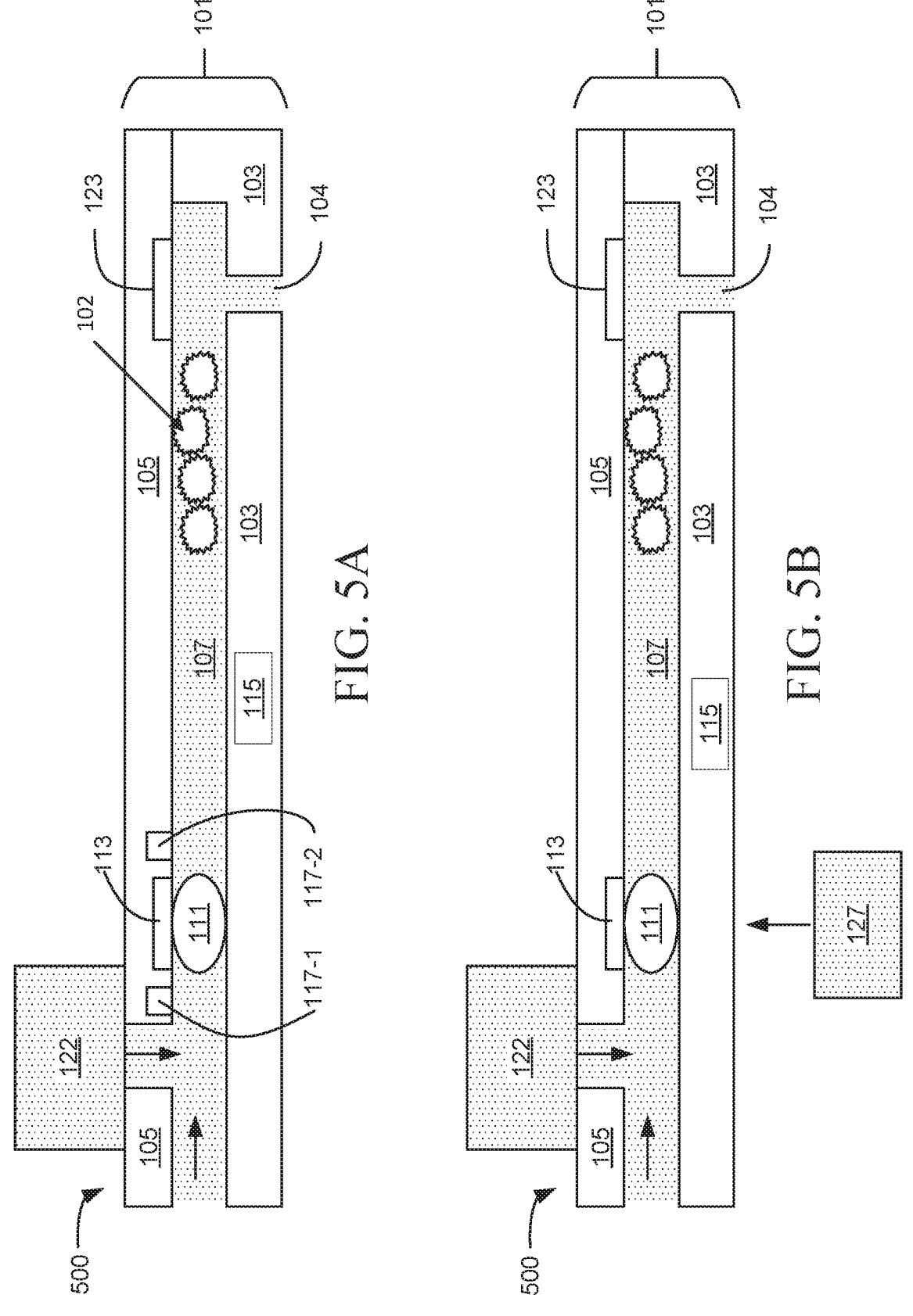
FIG. 5A illustrates an example apparatus with an external cell reservoir and an internal fluidic pump, according to the present disclosure.
FIG. 5B illustrates an example apparatus with an external cell reservoir, an internal fluidic pump, and external light source, according to the present disclosure.

FIGS. 5A and 5B illustrate example apparatuses with an external cell reservoir and an internal fluidic pump, according to the present disclosure. Particularly, FIG. 5A illustrates an example apparatus with an external cell reservoir and an internal fluidic pump, according to the present disclosure. The apparatus 500 illustrated in FIG. 5A includes an internal fluidic pump 123 disposed downstream from the cell detection element. Fluid flows from the cell reservoir 122, into the thermal cell lysis chamber 101. A cell 111 can be detected by the impedance sensors 117-1 and 117-2, and then heated by thermal lysing element 113. When the cell 111 is lysed, the cellular materials 102 may be dispensed via nozzle 104. Additionally, and/or alternatively to detecting cells within the microfluidic channel 107 using impedance sensors, cells may be detected within the microfluidic channel 107 using optical detectors as discussed with regards to FIG. 5B.

FIG. 5B illustrates an example apparatus with an external cell reservoir, an internal fluidic pump, and external light source, according to the present disclosure. Particularly, FIG. 5B illustrates an apparatus 500 in which the cell 111 may be detected within the microfluidic channel 107 using optical detectors. The apparatus 500 illustrated in FIG. 5B includes an internal fluidic pump 123 disposed downstream from the cell detection element. Fluid flows from the cell reservoir 122, into the thermal cell lysis chamber 101. A cell 111 can be detected using an externally placed light source 127 and photodetectors (not illustrated in FIG. 5B). The cell 111 is heated by thermal lysing element 113, and when the cell 111 is lysed, the cellular materials 102 may be dispensed via nozzle 104.

Figures 6A, 6B:
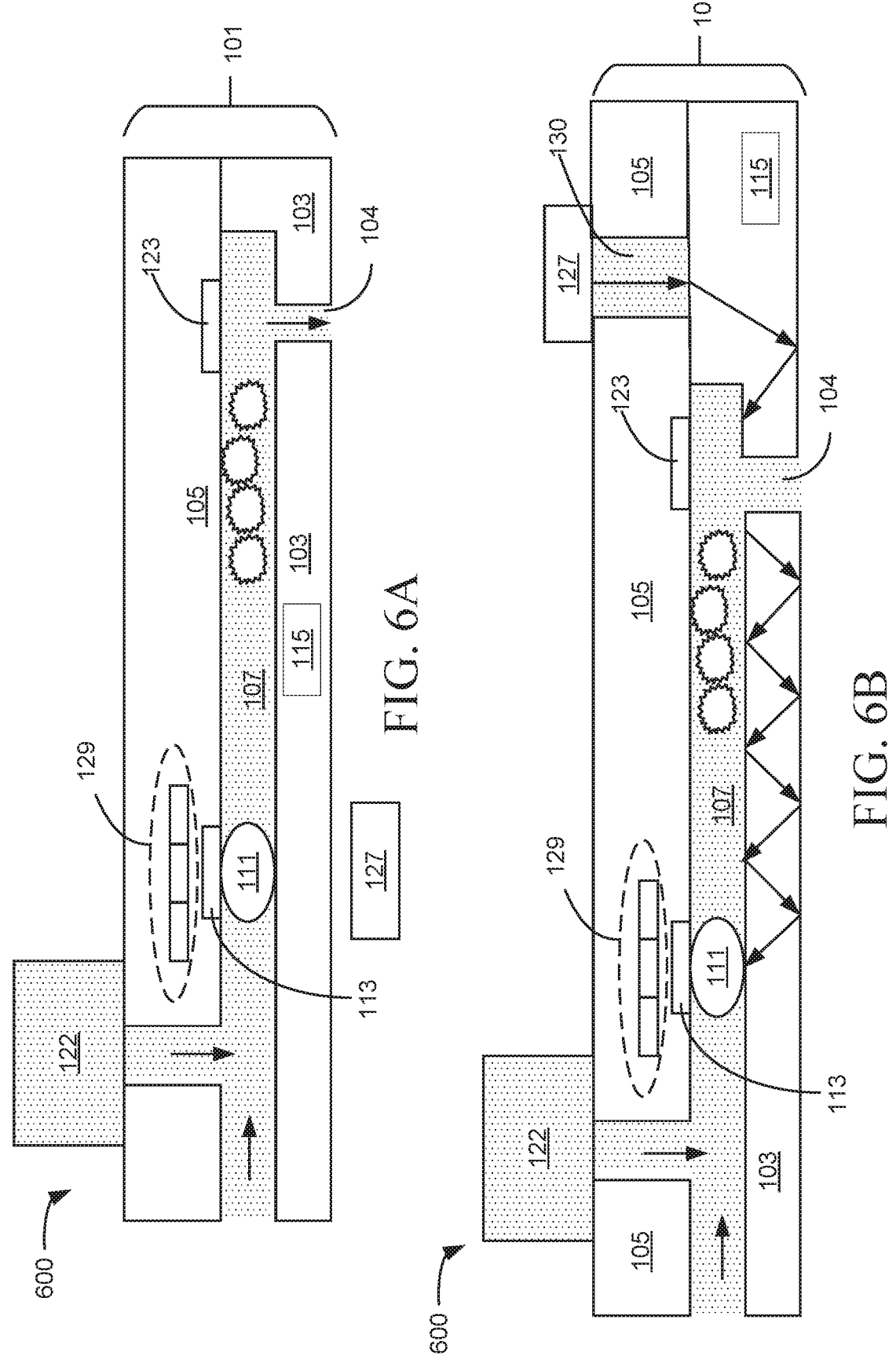
FIG. 6A illustrates an example apparatus including an integrated pump and integrated photodetector, according to the present disclosure.
FIG. 6B illustrates an example apparatus including an integrated pump and integrated photodetector, according to the present disclosure.

FIGS. 6A and 6B illustrate example apparatuses including a photodetector. Particularly, FIG. 6A illustrates an example apparatus including an integrated pump and integrated photodetector, according to the present disclosure. FIG. 6A illustrates an example apparatus 600 including a thermal cell lysis chamber 101 and a microfluidic channel 107. A light source 127 may direct light in a microfluidic channel 107. Presence of a cell 111 within the microfluidic channel 107 may be detected using a photodetector 129. Similarly, lysis of the cell 111 may be detected using the photodetector 129. A thermal lysing element 113 disposed within the lid 105 of the apparatus 600 may apply heat to the detected cell 111, as described herein. Particularly, lysis control circuitry 115 may regulate a temperature applied by the thermal lysing element 113, based on detection of a cell 111 within the microfluidic channel 107 and based on detection of a lysis event. The lysis control circuitry 115 may also record the temperature applied by the thermal lysing element 113 at which the lysis event occurred.

In various examples, the thermal lysing element 113 may be made of transparent conductive materials such as tin oxide, indium-tin oxide, zinc-tin oxide, and gallium-tin oxide among other transparent conductor materials. Transparent thermal lysing element 113 enables on die optical detection, such that the light source 127 can be placed externally or implemented in front side of the apparatus 600 above the thermal lysing element 113 without obscuring the detection of cell 111. Additionally, and/or alternatively, the light source 127 may be imbedded some distance away from the thermal lysing element 113 with light delivered to detection zone via waveguide, as discussed further herein.

FIG. 6B illustrates an example apparatus including an integrated pump and integrated photodetector, according to the present disclosure. Particularly, FIG. 6B illustrates the light source 127 positioned in a different location than illustrated in FIG. 6A. FIG. 6B illustrates the light source disposed on an opposite end of apparatus 600 from the cell reservoir 122. Light from the light source 127 is directed through opening 130 to the photodetectors 129 via a waveguide within the microfluidic channel 107. The waveguide may include plastic, glass, SUB, the microfluidic channel 107 or combinations thereof. In the example illustrated in FIG. 6B, the waveguide is the substrate 103. Light shines through the opening 130, into the substrate 103, reflects off opposing sides of the substrate 103, and illuminates the cell 111. The photodetectors 129 can then detect the surface of the cell 111 and monitor cell pore size for detection of a lysis event. As discussed herein, the lysis control circuitry 115 may slow a rate of temperature increase by the thermal lysing element 113 responsive to an increase in cellular pore size detected by a photodetector 129.

Figures 6C, 7A:
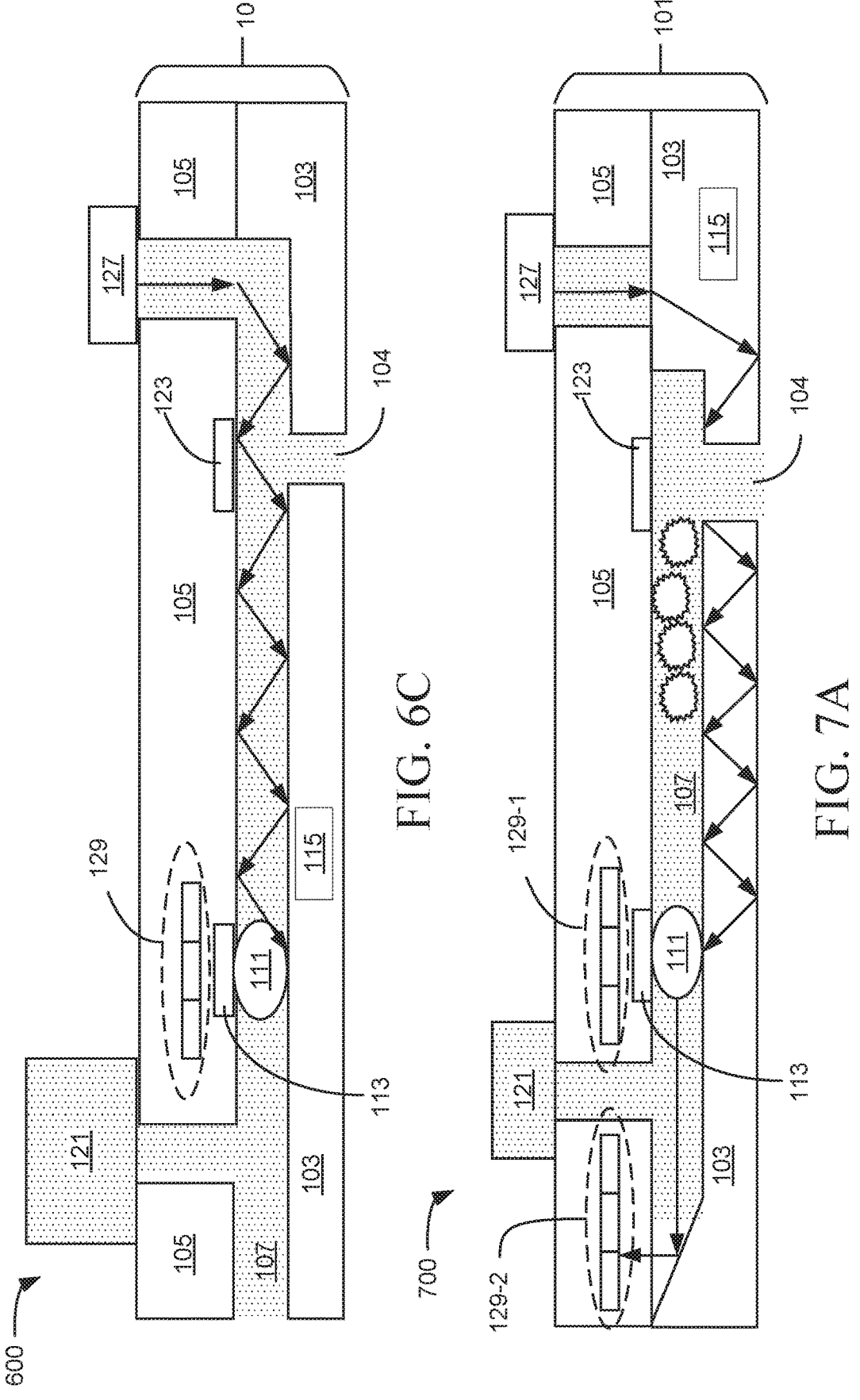
FIG. 6C illustrates an example apparatus including an integrated pump and integrated photodetector, according to the present disclosure.
FIG. 7A illustrates an example apparatus including an integrated pump and multiple photodetectors, according to the present disclosure.

FIG. 6C illustrates an example apparatus including an integrated pump and integrated photodetector, according to the present disclosure. In the example illustrated in FIG. 6C, the waveguide is the microfluidic channel 107. The light from light source 127 shines from the light source 127 through the opening 130, into the microfluidic channel 107, reflects off opposing sides of the microfluidic channel 107, and illuminates the cell 111. The photodetectors 129 can then detect the surface of the cell 111 and monitor cell pore size for detection of a lysis event.

FIG. 7A illustrates an example apparatus including an integrated pump and multiple photodetectors, according to the present disclosure. Particularly, FIG. 7A illustrates an example in which two photodetectors 129-1 and 129-2 are implemented. The light from the light source 127, may shine through the substrate 103, across the nozzle 104, and to the cell 111. Scattered light from the cell 111 may reflect to the photodetector 129-1. Similarly, scattered light from the cell 111 may reflect off an angled side of the substrate 103 and be detected by photodetector 129-2.

Figures 7B, 7C:
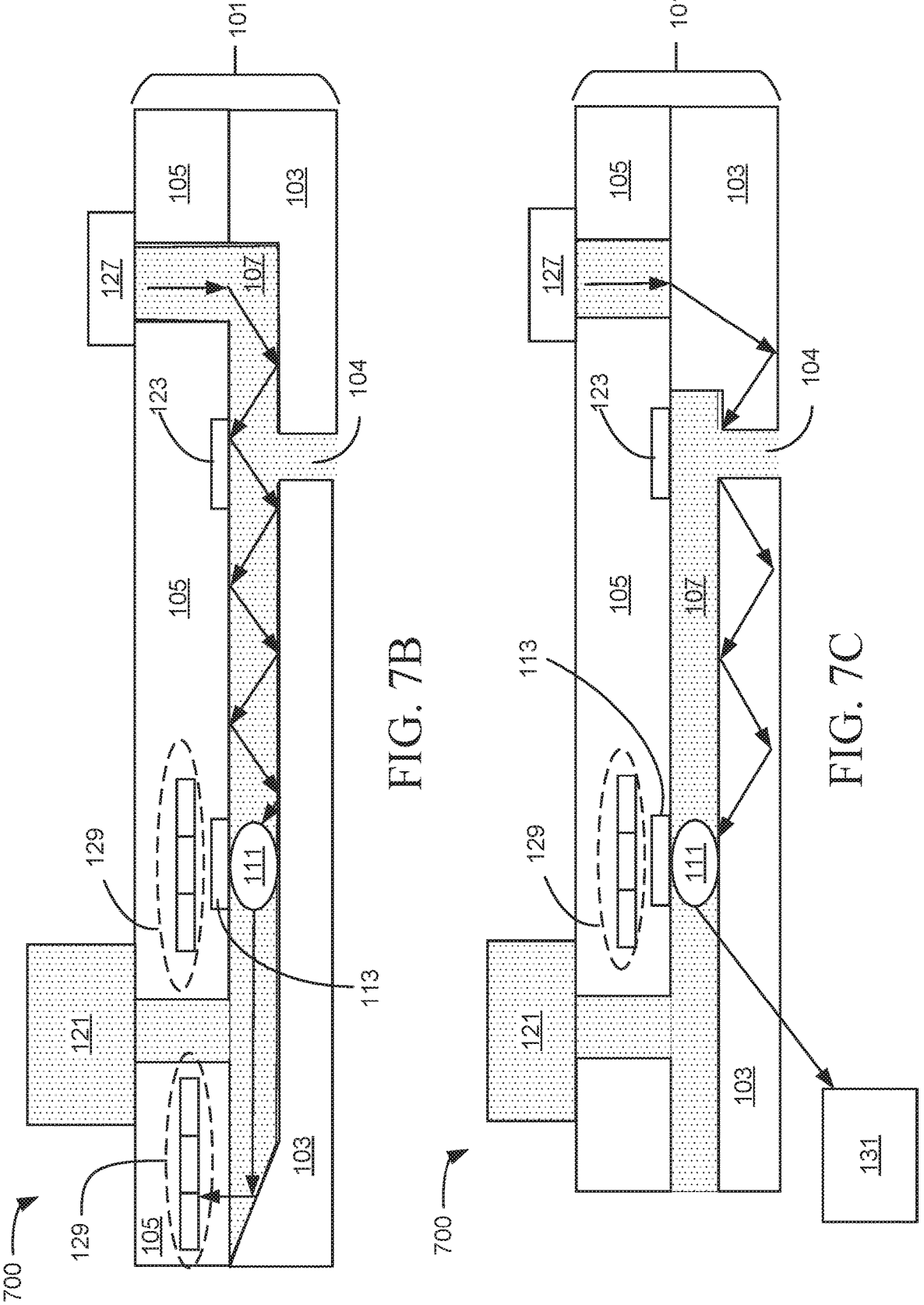
FIG. 7B illustrates an example apparatus including an integrated pump and multiple photodetectors, according to the present disclosure.
FIG. 7C illustrates an example apparatus including an integrated pump and an external photodetector, according to the present disclosure.

FIG. 7B illustrates an example apparatus including an integrated pump and multiple photodetectors, according to the present disclosure. Like the example illustrated in FIG. 7A, FIG. 7B illustrates an apparatus 700 including two photodetectors 129-1 and 129-2. In contrast to FIG. 7A, however, FIG. 7B illustrates the microfluidic channel 107 serving as a waveguide to direct light from the light source 127, through the microfluidic channel 107, to the cell 111. Light from light source 127 may pass from the cell 111 to the first photodetector 129-1 and reflect off an angled portion of the substrate 103 to a second photodetector 129-2. In some examples, additional and/or different photodetectors may be disposed outside of the apparatus 700 and be used to detect the presence of the cell 111, as discussed with regards to FIG. 7C

FIG. 7C illustrates an example apparatus including an integrated pump and an external photodetector, according to the present disclosure. In the example illustrated in FIG. 7C, light from the light source 127, may pass through the substrate 103, across the nozzle 104, and to the cell 111. Scattered light from the cell 111 may reflect to an external photodetector 131.

Figure 8A:
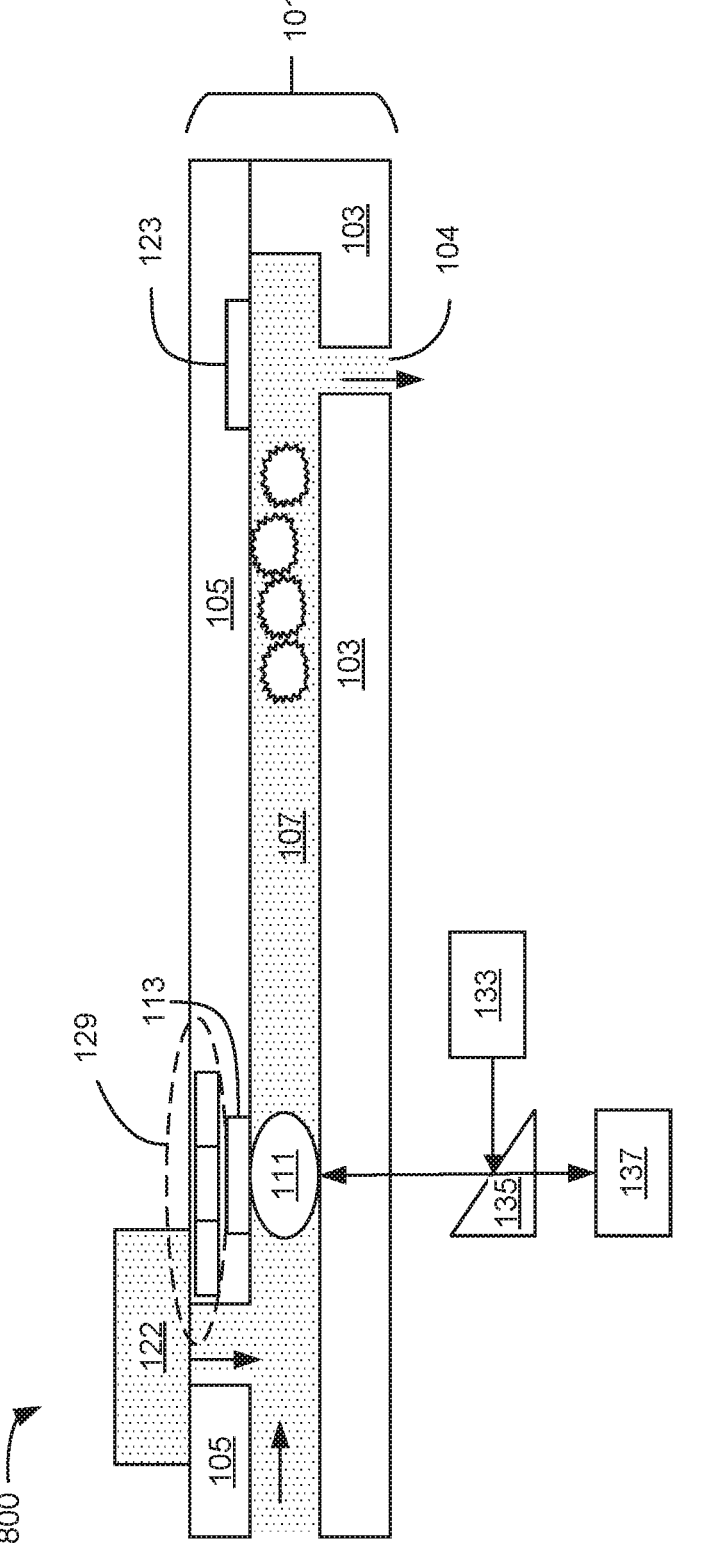
FIG. 8A illustrates an example apparatus including an integrated pump, an integrated photodetector, and an external photodetector, according to the present disclosure.

FIG. 8A illustrates an example apparatus including an integrated pump, an integrated photodetector, and an external photodetector, according to the present disclosure. In various examples, a plurality of photodetectors may be used to detect a cell within the microfluidic channel 107 and to detect a lysis event, as discussed herein. For instance, as illustrated in FIG. 8A, an external light source such as a laser 133 can reflect light off a beam splitter 135 and illuminate cell 111 in the microfluidic channel 107. An external photodetector 137 can detect light reflecting off the cell 111, and an internal photodetector 129 (e.g., embedded in the lid 105) can detect light reflecting off the cell 111 on a side opposite the external photodetector 137.

Figure 8B:
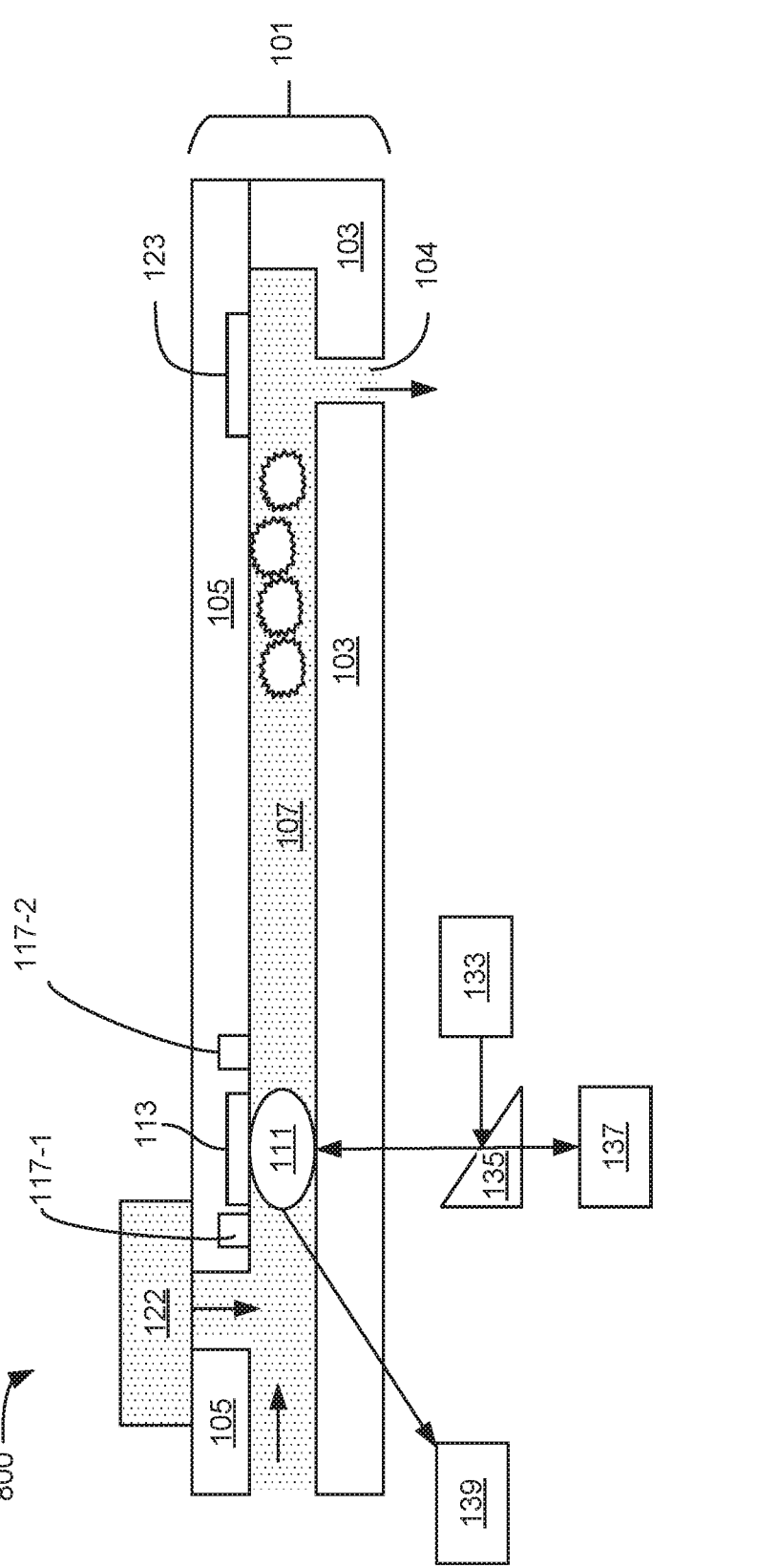
FIG. 8B illustrates an example apparatus including an integrated pump, and multiple sensors, according to the present disclosure.

FIG. 8B illustrates an example apparatus including an integrated pump, and multiple sensors, according to the present disclosure. As illustrated in FIG. 8B, both optical detection mechanisms and impedance sensors may be used to detect a cell in the microfluidic channel 107 and to observe cell lysis. Like FIG. 8A, an external light source such as a laser 133 can reflect light off a beam splitter 135 and illuminate cell 111 in the microfluidic channel 107. External photodetectors 137 and 139 can detect light reflecting off the cell 111. In addition, impedance sensors 117-1 and 117-2 may be disposed on opposing sides of thermal lysing element 113, such that the cell 111, and cell lysis, may be detected via the impedance sensors 117-1 and 117-2, as well as the optical elements.

Figure 8C:
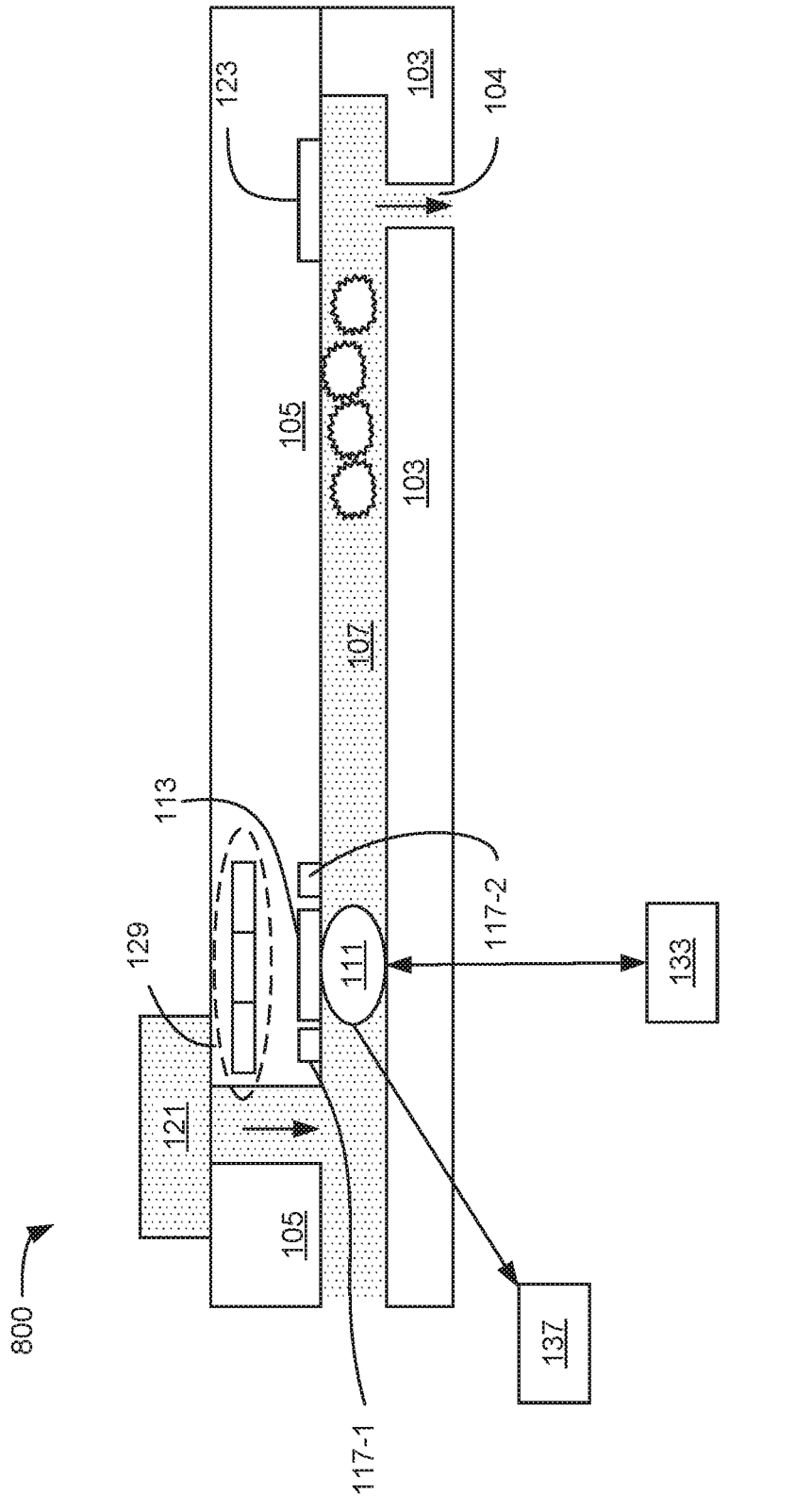
FIG. 8C illustrates an example apparatus including an integrated pump, and multiple sensors, according to the present disclosure.

FIG. 8C illustrates an example apparatus including an integrated pump, and multiple sensors, according to the present disclosure. As illustrated in FIG. 8C, both optical detection mechanisms and impedance sensors may be used to detect a cell in the microfluidic channel 107 and to observe cell lysis. Like FIG. 8A, an external light source such as a laser 133 can illuminate cell 111 in the microfluidic channel 107. An external photodetector 137 can detect light reflecting off the cell 111. In addition, impedance sensors 117-1 and 117-2 may be disposed on opposing sides of thermal lysing element 113, such that the cell 111, and cell lysis, may be detected via the impedance sensors 117-1 and 117-2, as well as the optical elements. Moreover, an internal photodetector 129 may detect light reflecting off the cell 111 for a multi-angled detection mechanism.

Figure 8D:
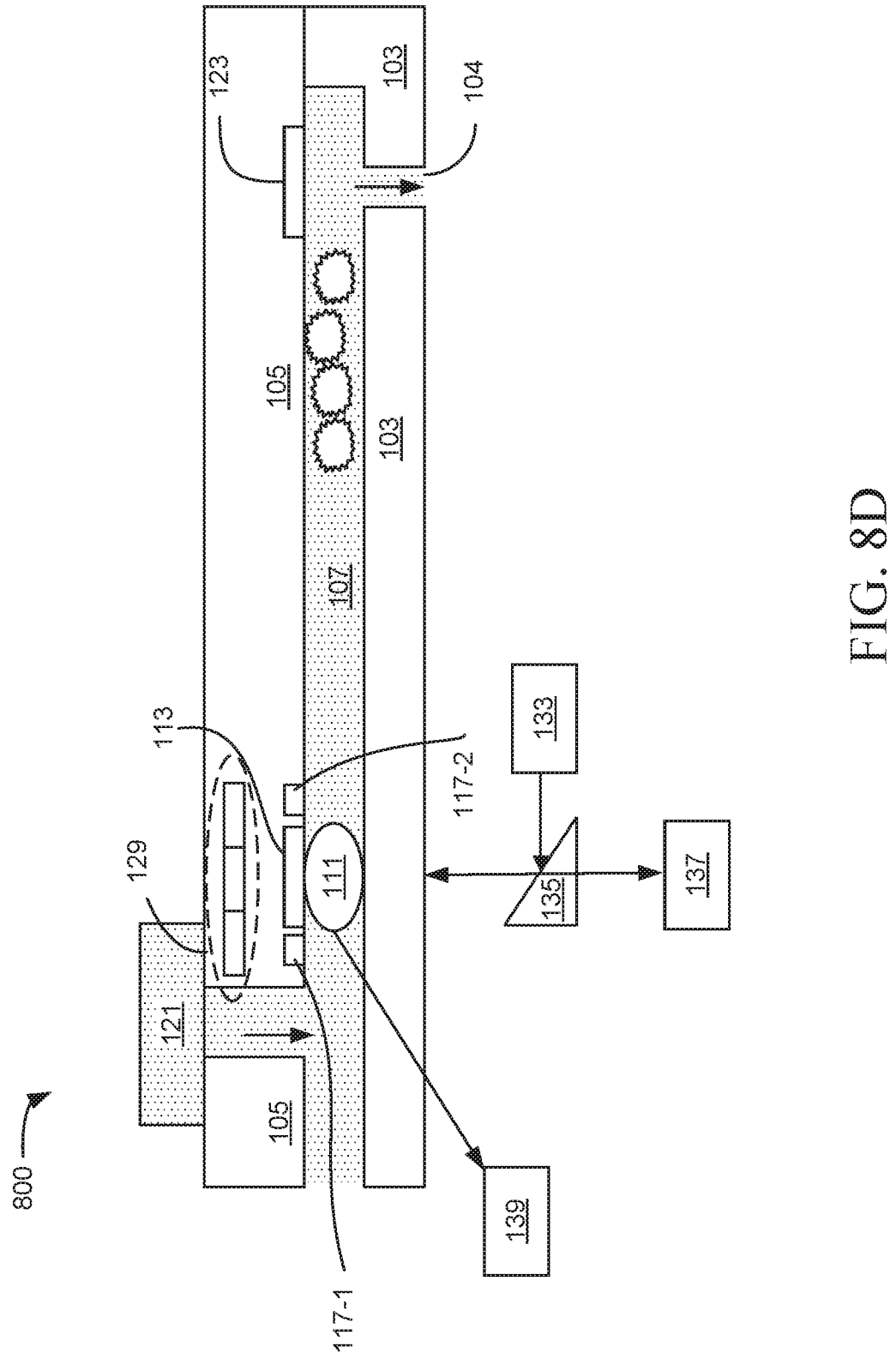
FIG. 8D illustrates an example apparatus including an integrated pump, and multiple sensors, according to the present disclosure.

FIG. 8D illustrates an example apparatus including an integrated pump, and multiple sensors, according to the present disclosure. As illustrated in FIG. 8D, both optical detection mechanisms and impedance sensors may be used to detect a cell in the microfluidic channel 107 and to observe cell lysis. Like FIG. 8B, both optical detection mechanisms and impedance sensors may be used to detect a cell in the microfluidic channel 107 and to observe cell lysis. An external light source such as a laser 133 can reflect light off a beam splitter 135 and illuminate cell 111 in the microfluidic channel 107. External photodetectors 137 and 139 can detect light reflecting off the cell 111. In addition, impedance sensors 117-1 and 117-2 may be disposed on opposing sides of thermal lysing element 113, such that the cell 111, and cell lysis, may be detected via the impedance sensors 117-1 and 117-2, as well as the optical elements. An internal photodetector 129 may detect light reflecting off the cell on an opposite side of the laser 133 for a multi-angle scattering mechanism.

Figure 9:
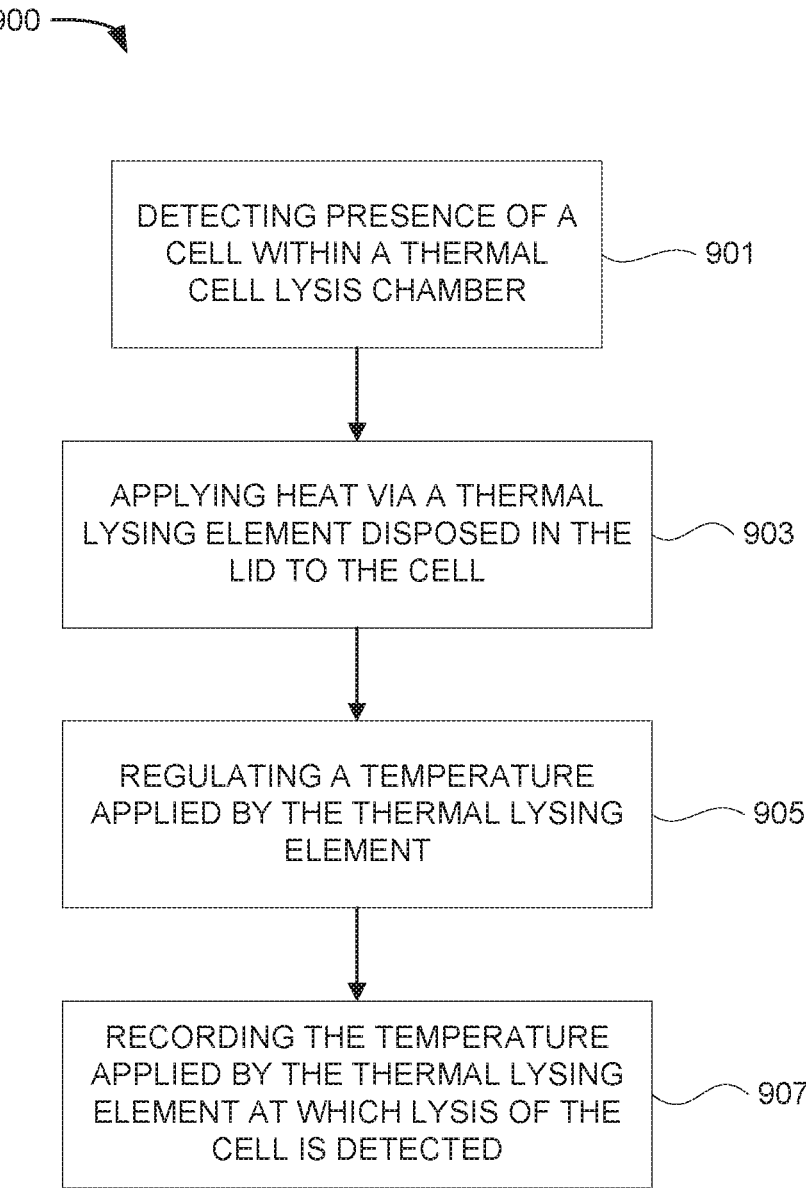
FIG. 9 illustrates an example method according to the present disclosure.

FIG. 9 illustrates an example method 900, according to the present disclosure. The method 900 at 901 includes detecting presence of a cell within a thermal cell lysis chamber. As discussed herein, the thermal cell lysis chamber includes a microfluidic channel, a substrate, and a lid coupled to the substrate. In various examples, the cell is detected via cell detection element in the lid of the thermal cell lysis chamber.

The method 900 at 903 includes applying heat via a thermal lysing element disposed in the lid to the cell detected by the cell detection element. At 905, the method 900 includes regulating a temperature applied by the thermal lysing element. In various examples, the temperature is regulated based on detection by the cell detection element of the cell within the microfluidic channel and based on detection by the cell detection element of a lysis event. At 907, the method 900 includes recording the temperature applied by the thermal lysing element at which lysis of the cell is detected.

In various examples, the method includes detecting the cell in the microfluidic channel by a photodetector disposed within the lid of the thermal cell lysis chamber. Additionally, the method may include decreasing a rate of temperature increase by the thermal lysing element responsive to an increase in cellular pore size detected by a photodetector disposed within the microfluidic channel. In such examples, the method includes directing light from a light source to the photodetector via a waveguide within the microfluidic channel. Additionally, and/or alternatively, the method 900 includes directing light from a light source to the photodetector via a waveguide within a substrate of the thermal cell lysis chamber.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein. Therefore, it is intended that this disclosure be limited only by the claims and the equivalents thereof.

The invention claimed is:

1. An apparatus, comprising:
   a thermal cell lysis chamber, including a substrate and a lid coupled to the substrate to form a microfluidic channel therethrough;

cell detection element to detect presence of a cell within the microfluidic channel and to detect lysis of the cell, the cell detection element including a pair of impedance sensors to detect the presence of the cell within the microfluidic channel responsive to a rapid increase in impedance measured by the pair of impedance sensors;

a thermal lysing element disposed in the lid between the pair of impedance sensors to apply heat to a cell detected by the cell detection element; and lysis control circuitry to:

regulate a temperature applied by the thermal lysing element, based on detection by the cell detection element of a cell within the microfluidic channel and based on detection by the cell detection element of a lysis event, wherein the lysis control circuitry is to regulate the temperature applied by the thermal lysing element at least by instructing the thermal lysing element to apply heat to the detected cell; and record the temperature applied by the thermal lysing element at which the lysis event occurred.

2. The apparatus of claim 1, wherein the cell detection element includes the pair of impedance sensors to detect lysis of a detected cell responsive to a rapid decline in impedance measured by the pair of impedance sensors.

3. The apparatus of claim 1, wherein the lysis control circuitry is to gradually increase the temperature applied by the thermal lysing element and record impedance across the microfluidic channel at each temperature applied by the thermal lysing element.

4. The apparatus of claim 1, wherein the cell detection element includes a photodetector to optically detect the presence of a cell within the microfluidic channel, and to detect a lysis event by visually observing rupture of the cellular membrane.

\* \* \* \* \*